United States Patent
Hung et al.

(10) Patent No.: US 9,066,793 B2
(45) Date of Patent: Jun. 30, 2015

(54) METHOD OF IMPLANTING AN AORTIC STENT

(71) Applicants: Yen-Ni Hung, Taipei (TW); Mao-Tsun Wu, Taichung (TW); Chen Yang, Taoyuan County (TW)

(72) Inventors: Yen-Ni Hung, Taipei (TW); Mao-Tsun Wu, Taichung (TW); Chen Yang, Taoyuan County (TW)

( * ) Notice: Subject to any disclaimer, the term of this patent is extended or adjusted under 35 U.S.C. 154(b) by 0 days.

(21) Appl. No.: 14/498,103

(22) Filed: Sep. 26, 2014

(65) Prior Publication Data

US 2015/0018942 A1    Jan. 15, 2015

Related U.S. Application Data

(63) Continuation-in-part of application No. 13/674,901, filed on Nov. 12, 2012, now abandoned.

(51) Int. Cl.
| | |
|---|---|
| *A61F 2/06* | (2013.01) |
| *A61F 2/07* | (2013.01) |
| *A61F 2/852* | (2013.01) |
| *A61F 2/856* | (2013.01) |

(52) U.S. Cl.
CPC . *A61F 2/07* (2013.01); *A61F 2/852* (2013.01); *A61F 2/856* (2013.01); *A61F 2002/065* (2013.01); *A61F 2230/001* (2013.01); *A61F 2230/0034* (2013.01); *A61F 2250/0039* (2013.01)

(58) Field of Classification Search
CPC ............. A61F 2/06; A61F 2/07; A61F 2/852; A61F 2/856; A61F 2/954; A61F 2002/061; A61F 2002/065; A61F 2250/0039
See application file for complete search history.

(56) References Cited

U.S. PATENT DOCUMENTS

| | | | |
|---|---|---|---|
| 7,014,653 B2* | 3/2006 | Ouriel et al. ................. | 623/1.14 |
| 2006/0155358 A1* | 7/2006 | LaDuca et al. ............... | 623/1.11 |
| 2013/0184806 A1* | 7/2013 | Arbefeuille et al. ......... | 623/1.11 |

* cited by examiner

*Primary Examiner* — Randy Shay
*Assistant Examiner* — Dinah Baria

(57) ABSTRACT

A method of implanting an aortic stent comprising steps of: putting a main tube on a metal guide wire; moving the main tube along the metal guide wire to the descending aorta, the main tube is constrained by a first cover, and first and second tube bifurcations are branched from the main section; removing the first cover; inserting a second and third metal guide wire through the first tube bifurcation into the ascending aorta and branchiocephalic artery respectively; a first and a second tube branch moving into the ascending aorta and the branchiocephalic artery respectively; inserting a fourth and fifth metal guide wire through the first tube bifurcation into the ascending aorta and branchiocephalic artery respectively; a third and a fourth tube branch moving into left common carotid artery and the left subclavian artery respectively; removing a second cover constraining said tube branches.

1 Claim, 8 Drawing Sheets

METHOD OF IMPLANTING AN AORTIC STENT

CROSS-REFERENCED TO RELATED APPLICATIONS

This application is a continuation-in-part of application Ser. No. 13/674,901 filed Nov. 12, 2012 entitled "Aortic Stent" and which is hereby incorporated herein by reference in its entirety.

STATEMENT REGARDING FEDERALLY SPONSORED RESEARCH OR DEVELOPMENT

Not applicable

BACKGROUND OF THE INVENTION

1. Field of the Invention

The invention relates to stents and more particularly to a method of implanting an aortic stent.

2. Description of Related Art

A conventional aortic stent is shown in FIG. 7. And the main stent 7 is disposed from ascending aorta (AA). As shown in FIG. 7, the length of ascending aorta is short and does not have a sufficient space. Also, there is no securing device for the main stent 7 and the main stent 7 may be movable. More importantly, when the main stent 7 is secured, it also takes time to secure the branch grafts into branchiocephalic artery (BA), common carotid artery (CCA), left subclavian artery (LSCA) and descending aorta (DA) before the blood can flow thereto. Meanwhile, if the main stent 7 moves when the blood flows therethrough, it may block the blood flow to either BA, CCA, LSCA or DA. Moreover, if it takes too long to dispose a plurality of stents 71,72,73,74, a permanent damage may be caused to the brain because of insufficient blood flow.

Furthermore, the way the main stent 7 is disposed in the ascending aorta cannot be achieved by a minimally invasive surgery. Actually, if utilizing the way to dispose the main stent 7, the doctor has to conduct a surgery to open up part of the sternum. Also, the way may cause Iatrogenic aortic dissection as shown in FIG. 8.

There are three portions in a cross section of a blood vessel from inside to outside: Tunica intima 6, Tunica media 5 and Tunica adventitia 4. When there is a cut on the inner wall of the blood vessel, the blood stream with high pressure is pouring into the cut and tearing the tunica intima 6 out of other layers of arterial wall, which can be a fatal complication. The blood flow could bi-directional intima flap and caused type A dissection. More seriously, the orifice of coronary artery that located at aortic rout would be obstruction by hematoma compression and leading fatal myocardial infarction.

Moreover, it is difficult to dispose the stent 74 as U shape as shown in FIG. 7.

Thus, the need for improvement still exists.

SUMMARY OF THE INVENTION

It is therefore one object of the invention to provide a method of implanting an aortic stent including a main tube and a plurality of tube branches comprising steps of:

putting a main tube on a metal guide wire, the metal guide wire is attached to one end of a needle which is disposed in the aorta;

moving the main tube along the metal guide wire to the descending aorta, the main tube is constrained by a first cover, and the main tube is bifurcated and comprises a main section having an outer diameter about equal to an inner diameter of a blood vessel of a descending aorta, and first and second tube bifurcations are branched from the main section; the first tube bifurcation includes a first membrane for dividing inside of the first tube bifurcation into a first space and a second space; the second tube bifurcation includes a second membrane for dividing inside of the second tube bifurcation into a third space and a fourth space ; the first space has an outer diameter, and said outer diameter of said first space, which corresponds to an inner diameter of an ascending aorta, is larger than outer diameters of the second space, the third space and the fourth space;

removing the first cover;

inserting a second metal guide wire through the first space into the ascending aorta, and a first tube branch moving along the second metal guide into the ascending aorta;

inserting a third metal guide wire through the second space into the branchiocephalic artery, and a second tube branch moving along the third metal guide into the branchiocephalic artery;

inserting a fourth metal guide wire through the third space into the left common carotid artery, and a third tube branch moving along the fourth metal guide into the left common carotid artery;

inserting a fifth metal guide wire through the fourth space into the left subclavian artery, and a fourth tube branch moving along the fourth metal guide into the left subclavian artery;

removing a second cover constraining said tube branches, wherein blood is configured to travel from the descending aorta and then to the main tube, the first space, the second space, the third space, and the fourth space.

The above and other objects, features and advantages of the invention will become apparent from the following detailed description taken with the accompanying drawings.

DETAILED DESCRIPTION OF THE INVENTION

Figure 1B:
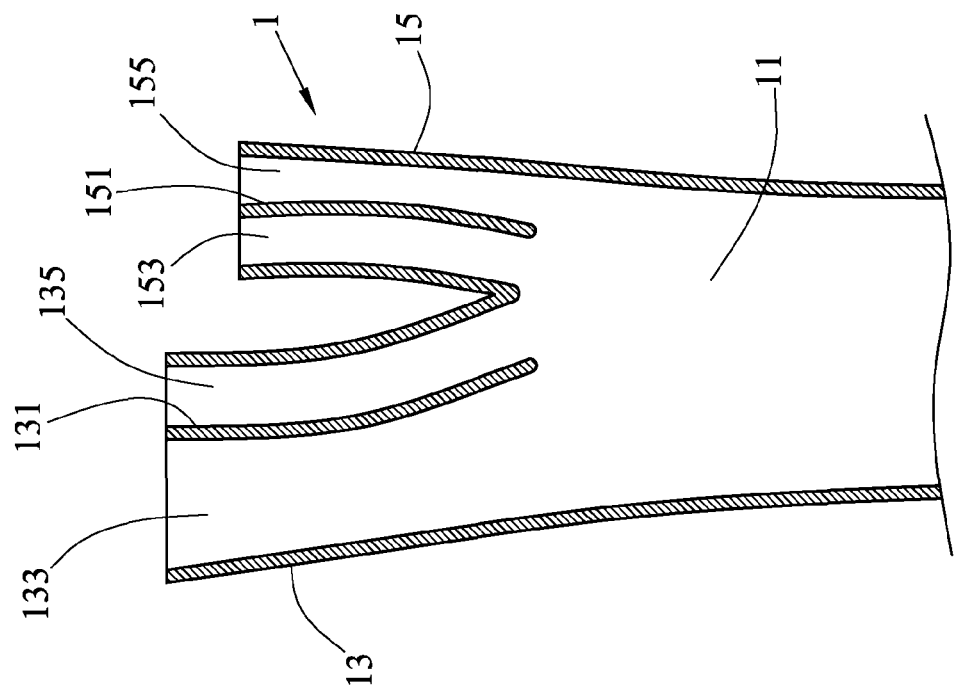
FIG. 1B is a longitudinal section view of the main tube.
Figure 1A:
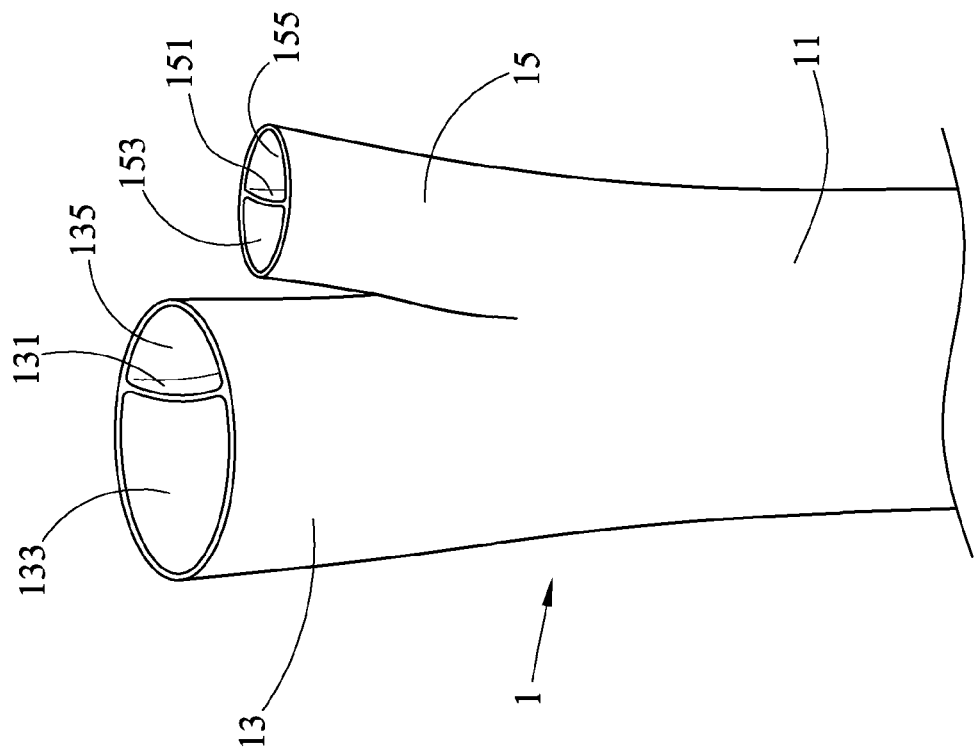
FIG. 1A is a perspective view of a main tube of an aortic stent according to the invention.
Figure 2:
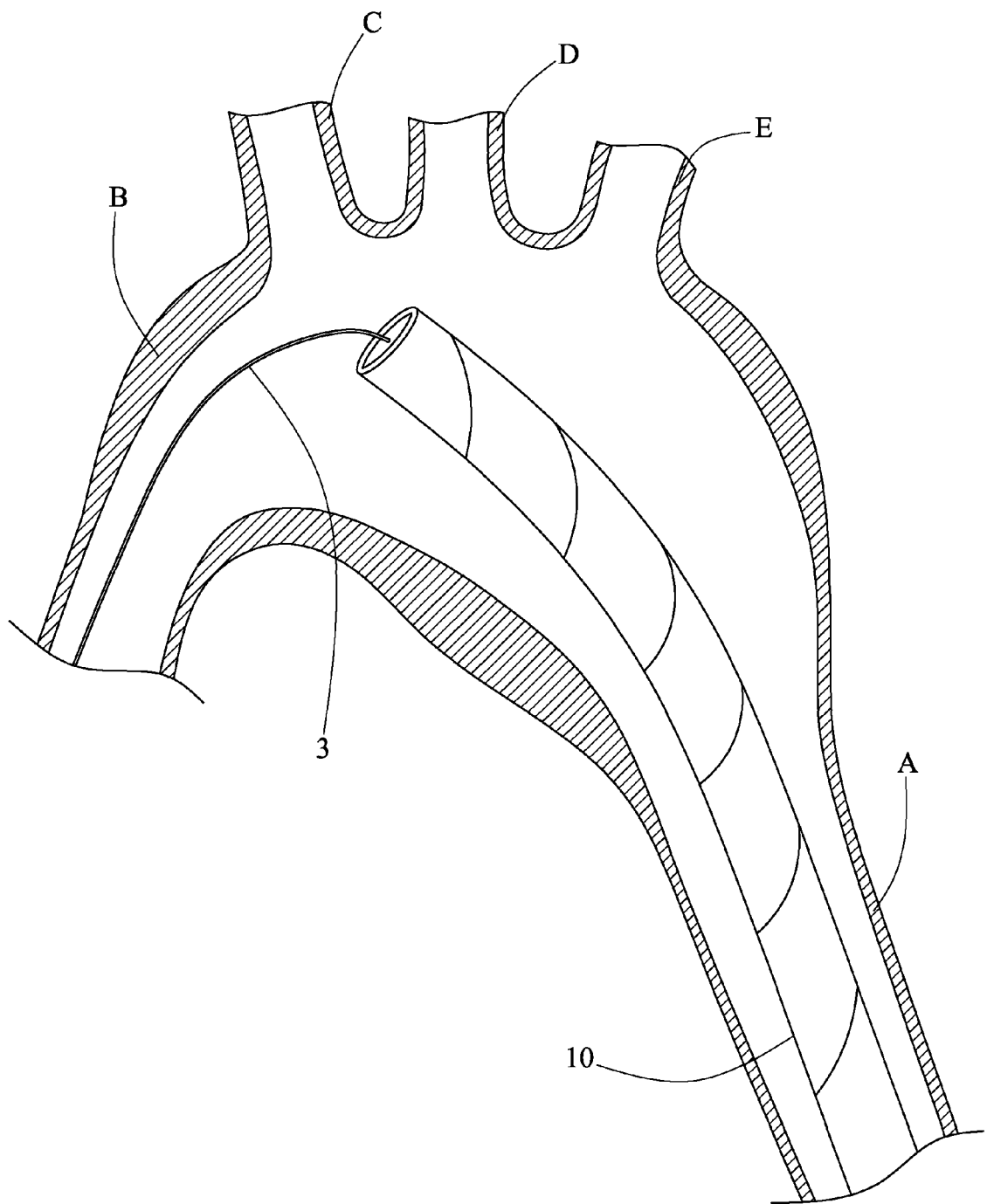
FIG. 2 is a longitudinal section view of a descending aorta with the main tube surrounded by a first cover being inserted into by using a metal guide wire.
Figure 3:
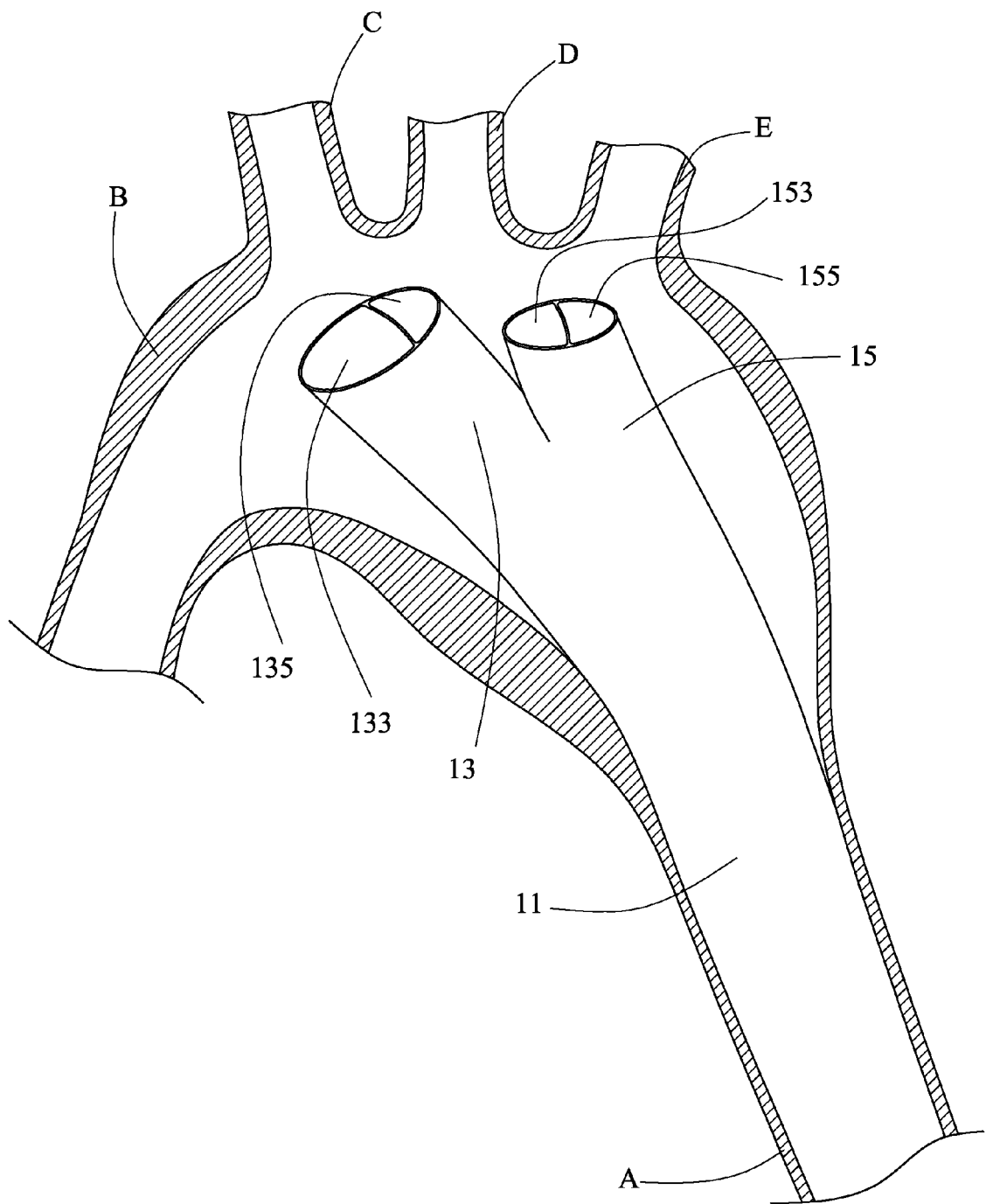
FIG. 3 is a longitudinal section view of the descending aorta with both the first cover and the metal guide wire being removed and the main tube being expanded to be retained in the descending aorta.
Figure 4:
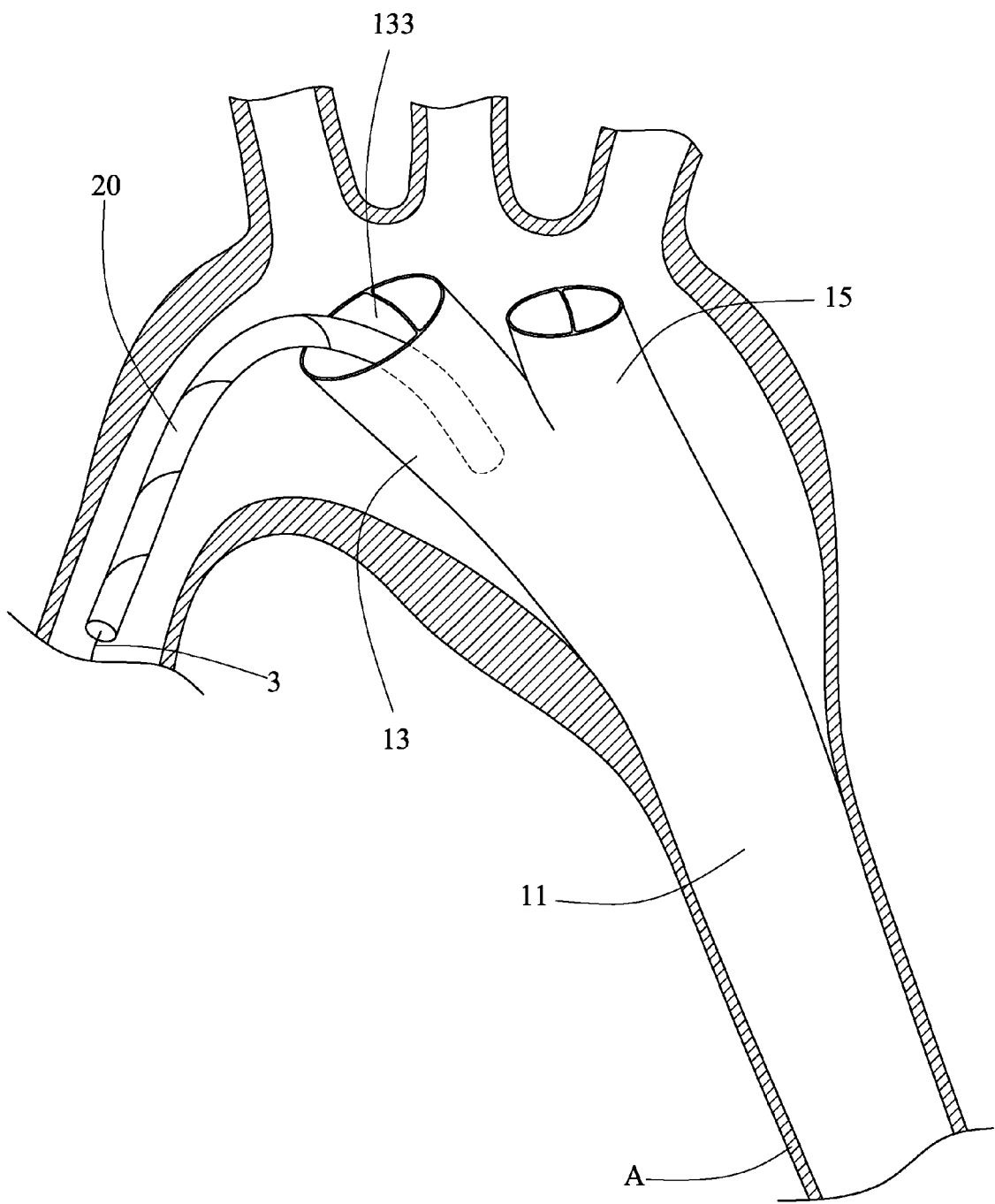
FIG. 4 is a view similar to FIG. 3 showing the insertion of a tube branch surrounded by a second cover into the main tube of FIG. 3.
Figure 5:
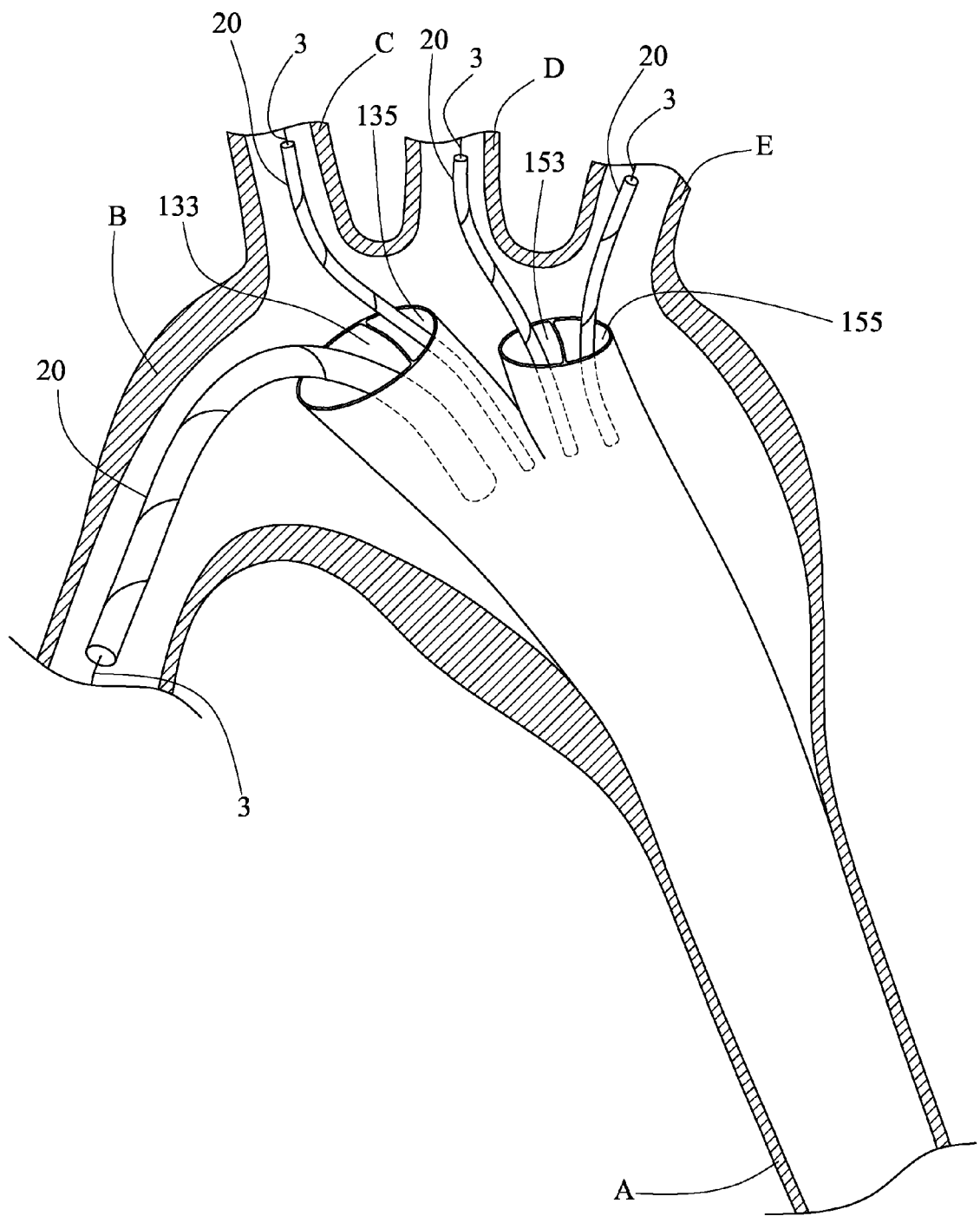
FIG. 5 is a view similar to FIG. 4 showing the insertion of additional three tube branches surrounded by second covers into the main tube of FIG. 3.
Figure 6:
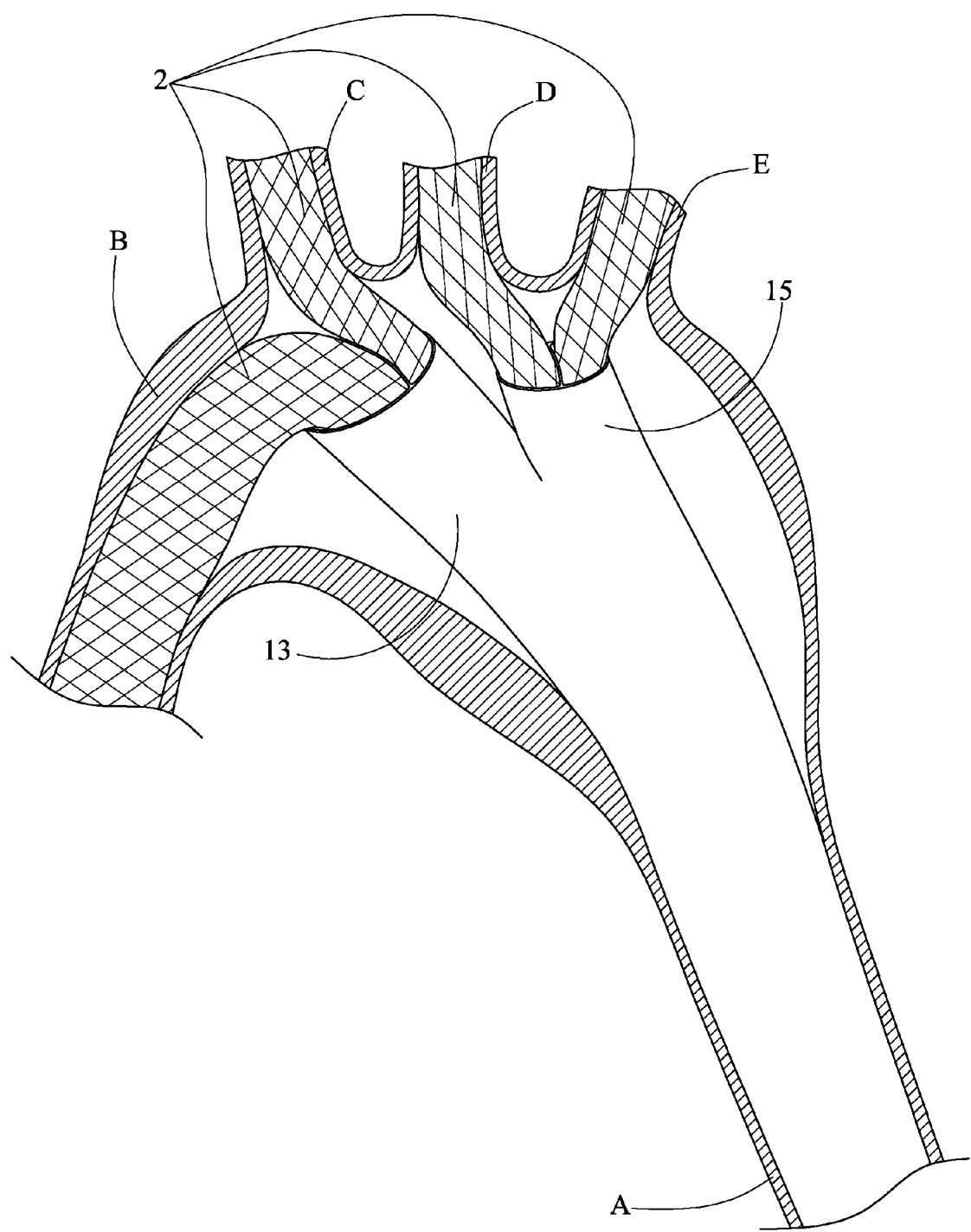
FIG. 6 is a view similar to FIG. 5 showing all second covers being removed and the tube branches being expanded to be retained in the descending aorta at the end of the aortic stent implantation.
Figure 7:
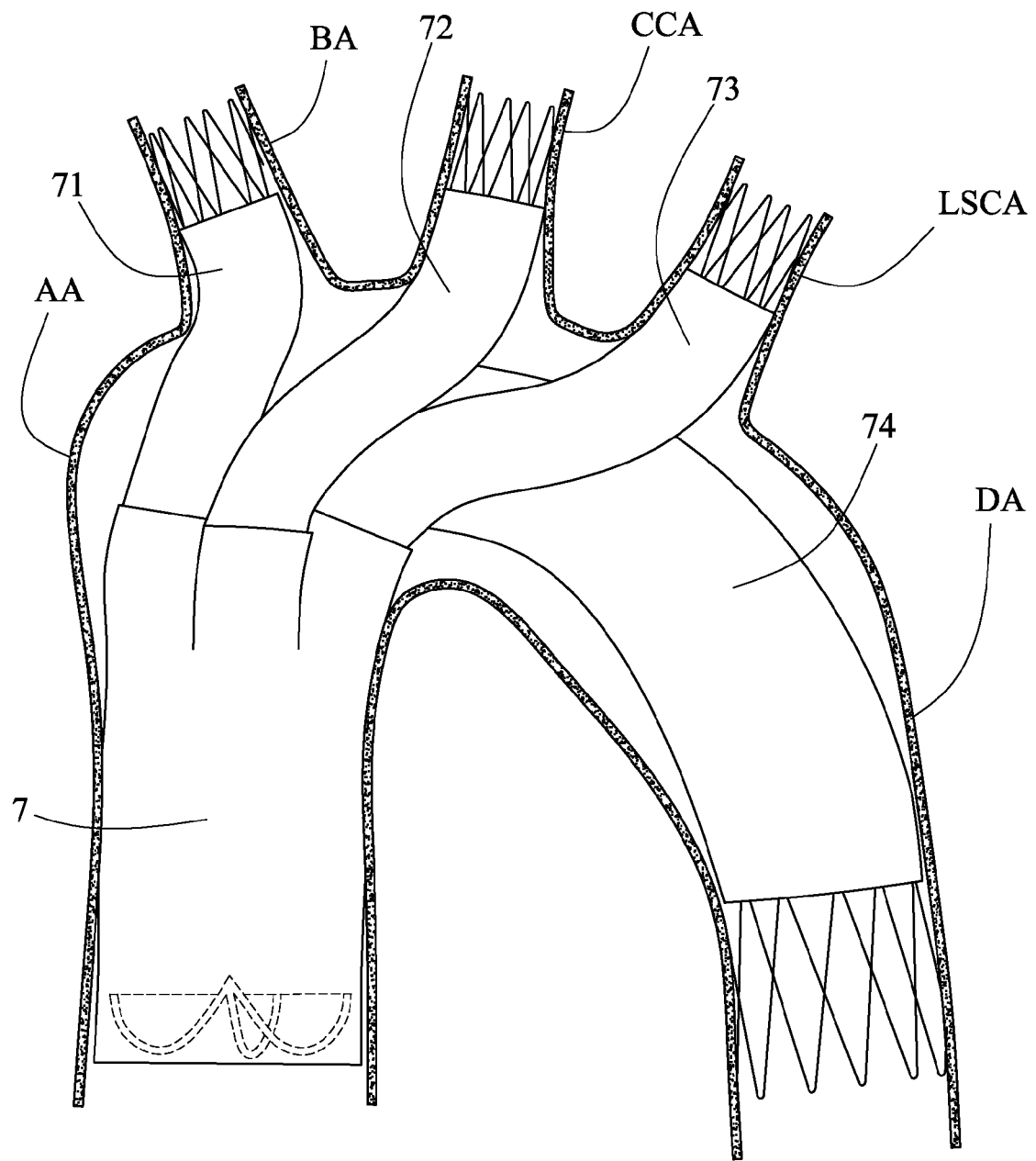
FIG. 7 is a multi-furcated endovascular prosthesis used to treat an ascending aortic aneurysm.
Figure 8:
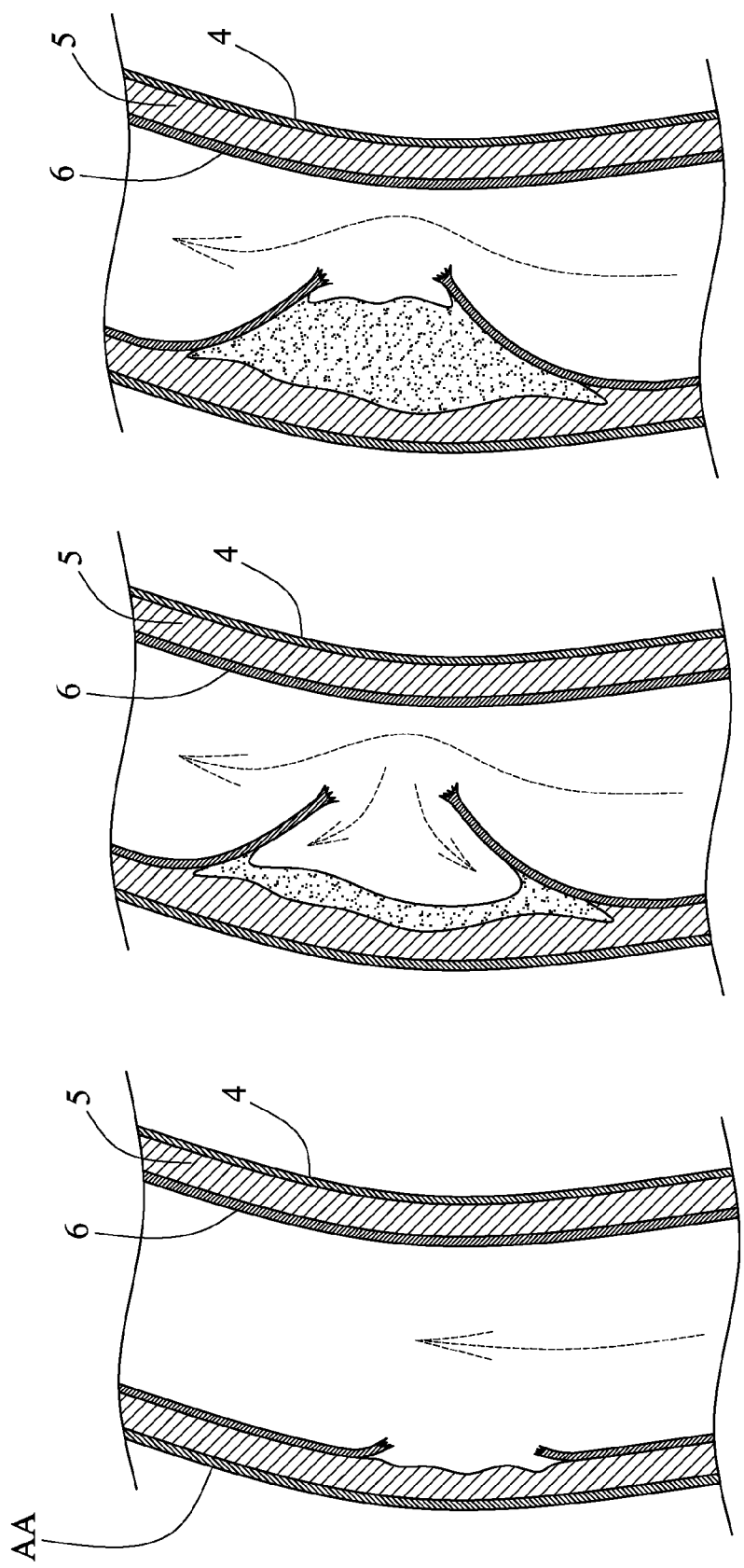
FIG. 8 is a longitudinal section view of a Iatrogenic aortic dissection.

Referring to FIGS. 1 to 6, an aortic stent in accordance with the invention comprises the following components as discussed in detail below.

A main tube 1 is bifurcated and comprises a main section 11 having an outer diameter about equal to an inner diameter of a blood vessel of a descending aorta A, and first and second tube bifurcations 13, 15 branched from the main section 11. The first tube bifurcation 13 includes a first membrane 131 for dividing inside of the first tube bifurcation 13 into a first space 133 and a second space 135. Likewise, the second tube bifurcation 15 includes a second membrane 151 for dividing inside of the second tube bifurcation 15 into a third space 153 and a fourth space 155. It is noted that the first space 133 has an outer diameter, and said outer diameter of said first space 133, which corresponds to an inner diameter of an ascending aorta, is larger than outer diameters of the second space 135, the third space 153 and the fourth space 155.

A plurality of (four are shown) tube branches 2 are adapted to hold in place in the first, second, third and fourth spaces 133, 135, 153 and 155 respectively so that the tube branches 2 may have one ends retained in the main tube 1 and the other ends in fluid communication with arteries.

The number of the tube branches 2 depends on positions of aortic aneurysm of a patient. Preferably, the number of the tube branches 2 is four. On ends of the tube branches 2 are disposed in the first, second, third and fourth spaces 133, 135, 153 and 155 respectively so as to connect to the main tube 1. The other ends of the tube branches 2 are disposed in ascending aorta B, branchiocephalic artery C, left common carotid artery D, and left subclavian artery E respectively. As such, blood from the descending aorta A may travel to the main tube 1 and in turn travel to the ascending aorta B, branchiocephalic artery C, left common carotid artery D, and left subclavian artery E in the first, second, third and fourth spaces 133, 135, 153 and 155 respectively.

The main tube 1 is surrounded by a first cover 10 and the tube branch 2 is surrounded by a second cover 20 respectively. Both the main tube 1 and the tube branch 2 are constrained by the first cover 10 and the second cover 20 respectively so that diameters of both the main tube 1 and the tube branch 2 are decreased. Both the main tube 1 and the tube branch 2 are expanded to restore blood flow paths after removing the first cover 10 and the second cover 20 respectively.

Steps of sequentially implanting the main tube 1 and the tube branch 2 are discussed in detailed below. First, the main tube 1 is put on a metal guide wire 3. Next, attach one end of the metal guide wire 3 to a needle which is in turn disposed in the aorta. Thus, the main tube 1 may move along the metal guide wire 3 to the descending aorta A (see FIG. 2). Next, remove the first cover 10 to expand the main tube 1 so that the main tube 1 may be retained in the descending aorta A (see FIG. 3).

Subsequently, insert a metal guide wire 3 through the first space 133 into the ascending aorta B. Next, one end of one of the tube branches 2 covered by the second cover 20 moves along the metal guide wire 3 into the ascending aorta B (see FIG. 4). Next, insert another metal guide wire 3 through the second space 135 into the branchiocephalic artery C. Next, one end of another tube branch 2 covered by the second cover 20 moves along the metal guide wire 3 into the branchiocephalic artery C. Likewise, insert still another metal guide wire 3 through the third space 135 into the left common carotid artery D. Next, one end of still another tube branch 2 covered by the second cover 20 moves along the metal guide wire 3 into the left common carotid artery D. Further, insert yet another metal guide wire 3 through the fourth space 155 into the left subclavian artery E. Next, one end of yet another tube branch 2 covered by the second cover 20 moves along the metal guide wire 3 into the left subclavian artery E. Above completes the implantation of the tube branches 2 (see FIG. 5).

Subsequently, the second covers 20 are removed from the main tubes 20 respectively so that the main tubes 20 may expand to be retained in the ascending aorta B, branchiocephalic artery C, left common carotid artery D, and left subclavian artery E respectively. As such, blood from the descending aorta A may travel to the main tube 1 and in turn travel to the first, second, third and fourth spaces 133, 135, 153 and 155 respectively (see FIG. 6). This is the end of the implantation of the aortic stent of the invention.

The invention has the following characteristics and advantages: The number of the tube branches 2 can be adjusted depending on positions of aortic aneurysm of a patient. The main tube 1 is disposed in the descending aorta A of the aorta. After the implantation, blood can travel to the ascending aorta B, branchiocephalic artery C, left common carotid artery D, and left subclavian artery E respectively via the main tube 1. This allows a physician to have sufficient time to implant the tube branches 2 in the aorta. Further, blood can smoothly travel to the ascending aorta B, branchiocephalic artery C, left common carotid artery D, and left subclavian artery E respectively via the main tube 1. That is, the aortic stent acts as a false lumen through which blood can travel, instead of flowing into the aneurysm sack. This can prevent the brain from being hurt because of insufficient blood flowing thereto. Finally, the physician may correctly implant the tube branches 2 in the aorta of a patient based on positions and shapes of the blood vessels to finish, for example, a vascular surgery. On the other hand, the stent in the present invention is disposed from descending aorta, which has a larger space to dispose the stent to ensure that the stent is not movable and does not block the blood flow.

While the invention has been described in terms of preferred embodiments, those skilled in the art will recognize that the invention can be practiced with modifications within the spirit and scope of the appended claims.

What is claimed is:

1. A method of implanting an aortic stent into a heart having an aorta, a descending aorta, an ascending aorta, a brachiocephalic artery, a left common carotid artery and a left subclavian artery, said stent including a main tube and a plurality of tube branches comprising steps of:

putting a main tube on a metal guide wire, the metal guide wire is attached to one end of a needle which is disposed in the aorta;

moving the main tube along the metal guide wire to the descending aorta, wherein the main tube is constrained by a first cover, and the main tube is bifurcated and comprises a main section having an outer diameter about equal to an inner diameter of a blood vessel of the descending aorta, and first and second tube bifurcations are branched from the main section; the first tube bifurcation includes a first membrane for dividing inside of the first tube bifurcation into a first tube branch having a first space and a second tube branch having a second space; the second tube bifurcation includes a second membrane for dividing inside of the second tube bifurcation into a third tube branch having a third space and a fourth tube branch having a fourth space; the first space has an outer diameter, and said outer diameter of said first space, which corresponds to an inner diameter of an ascending aorta, is larger than outer diameters of the second space, the third space and the fourth space;

removing the first cover;

inserting a second metal guide wire through the first space into the ascending aorta, and moving the first tube branch along the second metal guide into the ascending aorta;

inserting a third metal guide wire through the second space into the branchiocephalic artery, and moving the second tube branch along the third metal guide into the branchiocephalic artery;

inserting a fourth metal guide wire through the third space into the left common carotid artery, and moving the third tube branch along the fourth metal guide into the left common carotid artery;

inserting a fifth metal guide wire through the fourth space into the left subclavian artery, and moving the fourth tube branch along the fourth metal guide into the left subclavian artery;

removing a second cover constraining said tube branches, wherein blood is configured to travel from the descending aorta and then to the main tube, the first space, the second space, the third space, and the fourth space.

* * * * *